United States Patent [19]
Kang

[11] Patent Number: 5,874,296
[45] Date of Patent: Feb. 23, 1999

[54] METHOD AND APPARATUS FOR LIQUID MEDIUM EXCHANGE

[76] Inventor: Jing X. Kang, 28 Meadowood Rd., North Andover, Mass. 01845

[21] Appl. No.: 7,453

[22] Filed: Jan. 15, 1998

[51] Int. Cl.⁶ .................................................. C12M 1/26
[52] U.S. Cl. .................................... 435/283.1; 435/309.1; 422/100; 141/65; 604/902; 73/864.12; 73/864.15
[58] Field of Search ............................. 435/286.4, 286.5, 435/283.1, 309.1, 309.2; 422/100; 604/33, 34, 35, 902; 73/864.11, 864.12, 864.15, 864.22; 141/65, 249; 137/102, 596; 222/158, 191, 205, 425, 441, 449; 433/91, 95

[56] References Cited

U.S. PATENT DOCUMENTS

| | | |
|---|---|---|
| 2,732,985 | 1/1956 | Howard . |
| 4,015,942 | 4/1977 | Coupe . |
| 4,198,482 | 4/1980 | Homer . |
| 4,635,665 | 1/1987 | Namba et al. . |
| 4,685,480 | 8/1987 | Eck . |
| 4,754,771 | 7/1988 | Tangherlini et al. . |
| 5,120,305 | 6/1992 | Boehringer et al. . |
| 5,542,918 | 8/1996 | Atkinson . |

*Primary Examiner*—William H. Beisner
*Attorney, Agent, or Firm*—Scott B. Garrison; Lambert & Garrison PLLC

[57] ABSTRACT

The purpose of this invention is to provide a novel apparatus capable of suctioning a liquid from a container by using a vacuum. Simultaneously, the vacuum draws a second liquid from a separate source to fill a reservoir which forms part of the apparatus. Once the first liquid is drawn and the reservoir is filled with the second liquid, vacuum is disengaged by releasing a normally open vacuum control. Further disengaging of a normally closed reservoir control allows the second liquid to drain from the reservoir into the now empty container which formerly contained the first liquid. Use of this apparatus significantly eases the task of changing liquid culture mediums since the operator can now accomplish the task in essentially one step thereby minimizing potential contamination to the second liquid, the culture, and the environment.

18 Claims, 5 Drawing Sheets

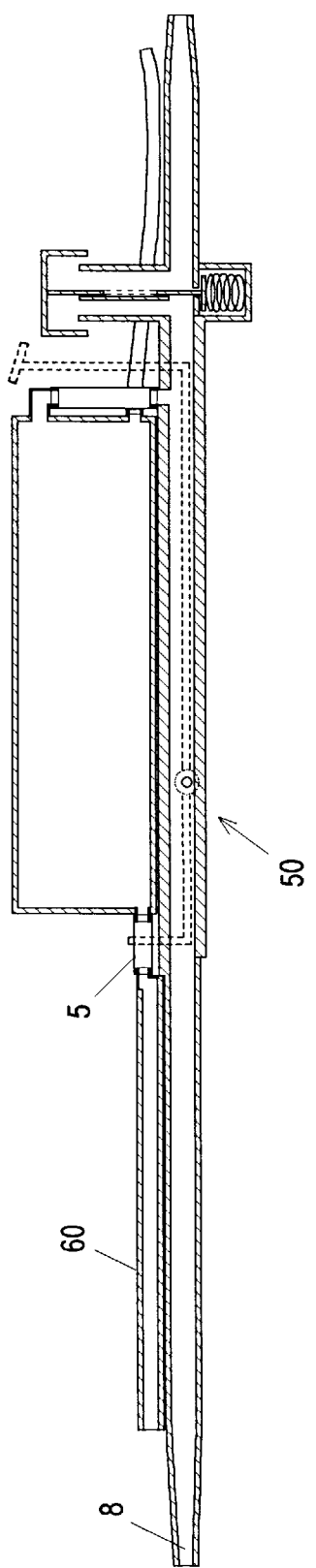

METHOD AND APPARATUS FOR LIQUID MEDIUM EXCHANGE

BACKGROUND OF THE INVENTION

The present invention relates to the field of biological cellular cultures. More particularly, it relates to a novel apparatus and method for changing a liquid culture medium used to cultivate cell cultures with a new medium.

Changing culture medium is a routine and heavy job of isolated cell culture, and needs to be performed every other day. Traditionally, the procedures of changing culture medium include at least two separate steps:

1) Aspiration or removal of the old medium from a culture vessel by means of vacuum suction or pipetting; a process of dipping an open-ended tube into the liquid medium, and withdrawing the tube and liquid within the tube from the medium for disposal.

2) Addition of new medium to the culture vessels using another tool, usually a pipette, to transfer medium from a liquid container to the culture vessels.

Generally, the process for the conventional operation of changing medium is described below. If using a vacuum means; aspirate the old medium, change the tool, draw the new medium, and release the new medium to the culture vessels. If pipetting; draw the old medium, dispose of it, draw new medium, and release the new medium to the culture vessels. The operator may or may not change pipettes to isolate the new medium from potential intermixing of residue from the old medium contained within the pipette.

These procedures involve many actions, multiple pauses, frequent opening of culture vessels and medium containers. Furthermore the potential exists for the prolonged exposure of cultured cells to air, particularly when a large volume of medium or a large number of vessels need to be changed. Therefore, the process is time consuming in the least and potentially harmful to the cultured cells due to their prolonged exposure to air as well as significantly increasing the risk of contamination due to the repetitive actions necessary.

SUMMARY OF THE INVENTION

As such it is a principle object of the present invention to provide a novel apparatus for changing culture medium conveniently, efficiently and safely.

Another object of the present invention is to provide a medium-changing tool capable of continuously removing old medium from a culture vessel while concurrently refilling the culture vessel with new medium without requiring the operator to change tools or suffer any pause or delay in the operation.

Another object of the invention is to provide a medium-changing tool capable of greatly reducing the overall consumption of time associated with conventional medium-changing procedures.

A further object of the invention is to provide a medium changing tool that can simplify the operational procedures and eliminate the repetitive opening of cell culture vessels and medium containers, thereby reducing the risk of cell contamination.

A still further object of the present invention is to provide a medium changing tool capable of shortening the time interval between removal of old medium and replacement of medium, thereby reducing the potential harm to cultured cells.

An even further object of the invention is to provide a medium changing tool that is economical and able to reduce the material waste conventional medium-changing produces.

In addition, this apparatus can be also used as a solution dispenser.

The above and still further objects, features and advantages of the present invention will become more apparent as this description proceeds.

The manner with which the Applicant has accomplished these objectives and solved the aforementioned problems is to invent a unique and novel vacuum operated apparatus. The apparatus essentially comprises a pipe for transferring old medium out of a first container, for instance, a culture vessel and replacing the old medium with new medium. Attached to the pipe is a reservoir to contain the new medium prior to its ultimate transfer to the culture vessel. The pipe is connected at one end to a vacuum source and through the manipulation of a vacuum controller, the old medium is aspirated or sucked from the culture vessel through the pipe to an appropriate disposal receptacle. Simultaneously new medium is sucked from a source of new medium and deposited into the reservoir. When the old medium is completely extracted and sufficient new medium fills the reservoir, the vacuum controller is disengaged thereby stopping fluid transfer and eliminating the vacuum. Activation of another controller allows the medium reservoir to be drained by gravity into the cell culture vessel.

BRIEF DESCRIPTION OF THE DRAWINGS

The novel features considered characteristic of the invention are set forth in the appended claims. The invention itself, however, both as to its construction and its method of operation, together with additional objects and advantages thereof, will best be understood from the following description of the specific embodiments when read and understood in connection with the accompanying drawings.

FIG. 5 is a perspective view of an alternative configuration of the FIG. 1 device, this one depicting a second pipe connected to the reservoir.

DETAILED DESCRIPTION OF THE PREFERRED EMBODIMENT

Figure 1:
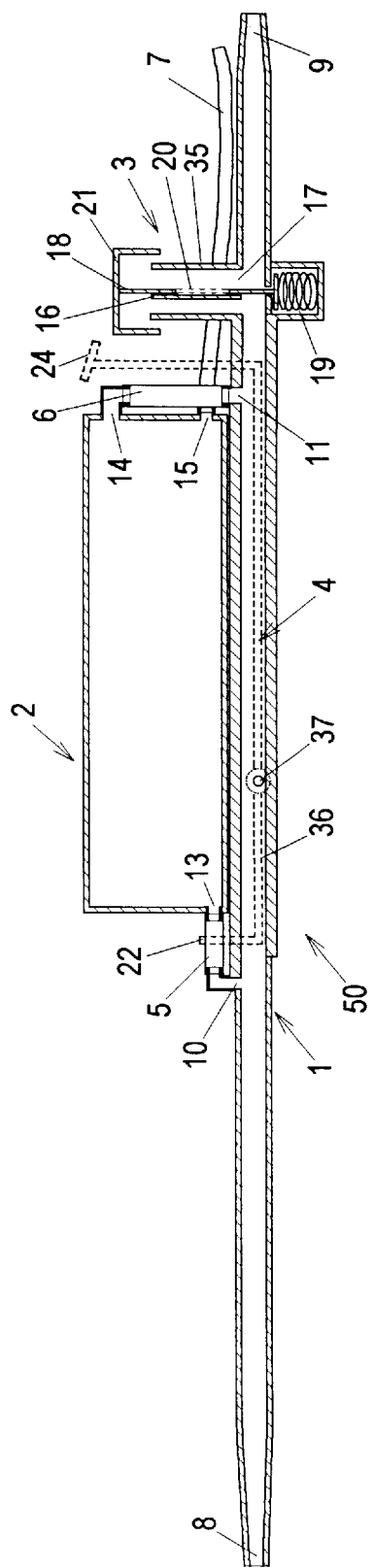
FIG. 1 depicts a cutaway through the center of a preferred embodiment of a liquid medium exchange apparatus in accordance with the present invention.
Figure 2:
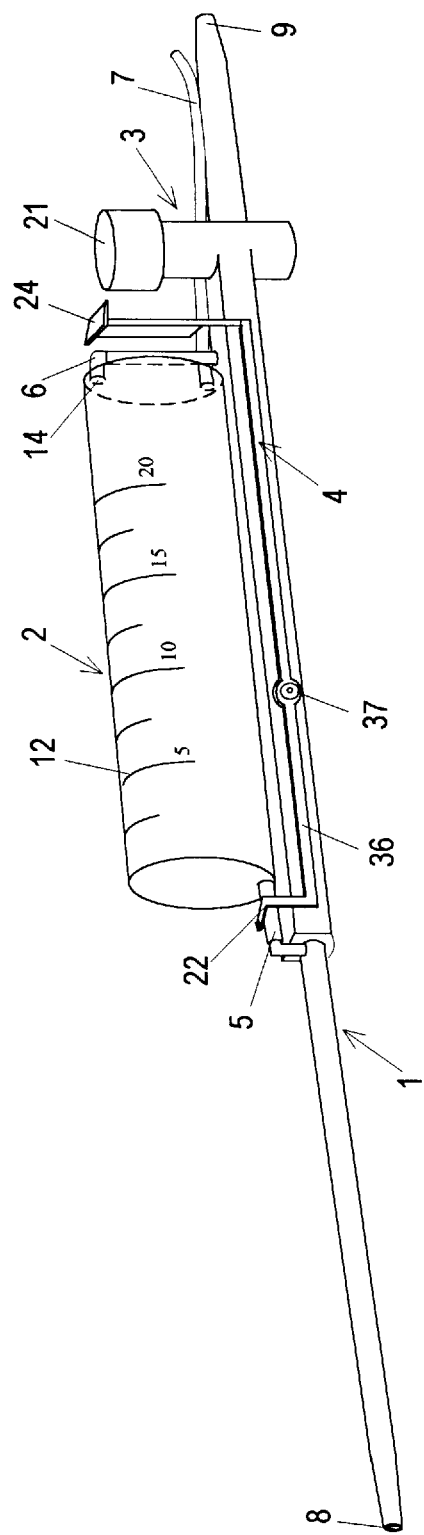
FIG. 2 depicts a perspective view from the front toward the rear of the FIG. 1 apparatus.
Figure 3:
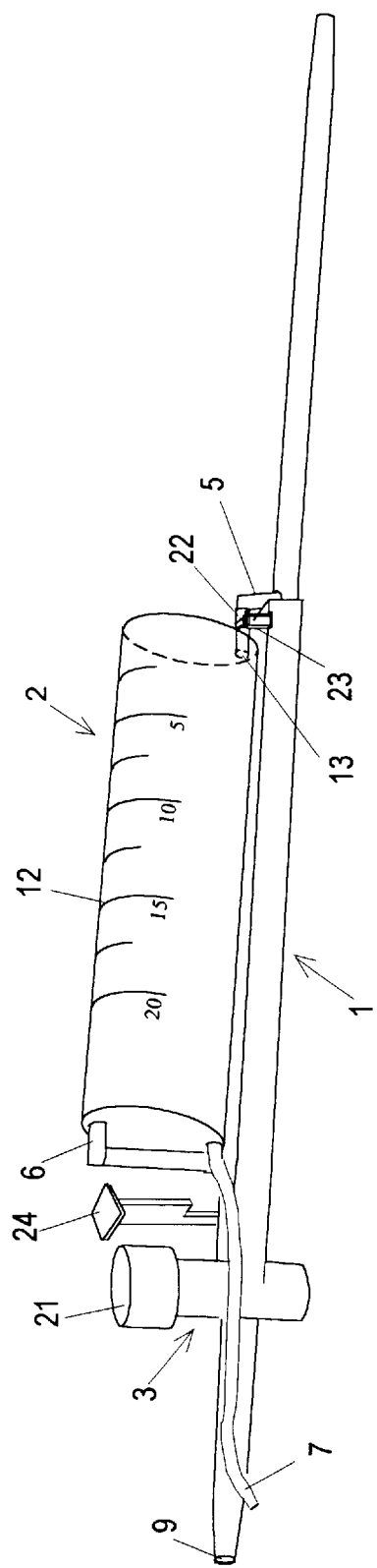
FIG. 3 depicts a view similar to FIG. 2 but from the rear toward the front.

With reference to FIGS. 1, 2 and 3, a preferred embodiment of a liquid medium exchange apparatus 50 is depicted. The apparatus primarily comprises a pipe 1, a cylinder reservoir 2, a vacuum controller 3, a reservoir control 4 and associated connecting tubing 5, 6, and 7. The pipe 1 has a first end preferably tapered into an opening tip 8 which is used for the drawing and delivery of a liquid medium, a central portion, and a second end comprising an opening 9 for connection to a vacuum source. The second end further provides a convenient handle for an operator to hold the apparatus. The central portion of pipe 1 is configured to cradle or otherwise hold the cylinder reservoir 2 in intimate contact thereto. Additionally, at a forward and a rearward end of the central portion of pipe 1 are located access openings 10 and 11 respectively. Access opening 10 is connected to a corresponding opening 13 in the forward end of the cylinder 2 via tubing 5. The access opening 11 is connected to a corresponding opening 14 in the rearward end of the cylinder 2 via tubing 6. The vacuum controller 3 is disposed between the access opening 11 and the opening 9 of pipe 1.

The cylinder 2 has a third opening 15 which is attached to a new liquid source which is intended to be placed in the culture vessel. Though other means could be used to accomplish the same purpose, the respective heights of each of these openings 13, 14, and 15 in relation to that portion of the cylinder in contact with the pipe 1 perform a useful role in the function of the apparatus. As can be seen in the FIGS., in the preferred embodiment of the cylinder 2, openings 13 and 15 are placed low in the cylinder, whereas opening 14 is placed substantially higher. The reasons for this are clarified below by the discussion of how the apparatus works.

Looking first more specifically at FIG. 1, the vacuum controller 3 is seen to comprise a housing 35 suitably configured to receive a seal cap 21. The seal cap 21 provides a convenient on-off means to control the vacuum with which the apparatus 1 is subjected. The seal cap 21 is normally displaced from the housing 35. By causing the seal cap 21 to seal with the housing 35, vacuum can be built up and maintained within the apparatus. Whereas releasing seal cap 21 breaks the vacuum. Though certainly not the only structure able to perform the operation, the applicant's preferred configuration of the vacuum controller 3 includes dividing the housing 3 into two individual passages or channels 17 via a dividing wall 16. By adding a sliding partition 18 containing a passage 20 to the seal cap 21, the passage 20 can be made to align or non-align with an internal passage of pipe 1. A biasing means such as spring 19 can be utilized to keep the seal cap 21 in its normally open position.

In order to complete the preferred embodiment, FIGS. 2 and 3 depict the reservoir control 4 which enables the new liquid medium to be drained from the cylinder reservoir 2. The reservoir control 4 comprises a lever 36 pivotally attached to the pipe 1 by a pin connection 37. A forward portion 22 of the lever 36 is made to overlie the tubing 5. This overlapping forward portion 22 of the lever 36 impinges upon tubing 5 thus pinching off or clamping the tubing 5 between the forward portion 22 and the pipe 1. To assist in this, a biasing means such as a rubber band 23, spring or other suitable mechanism is utilized to keep portion 22 firmly clamped against the tubing 5 thereby eliminating flow. It should be obvious that the tubing 5 by necessity must be made sufficiently soft so as to be collapsible upon itself for the embodiment just described to work. However, other means could be satisfactorily adapted to accomplish the same result. One such means that comes to mind is a partition type arrangement as described previously for the vacuum controller 3. Nonetheless, to enable flow through the tubing 5, a rearward portion of the lever 36 ends in a paddle 24 or an equivalent user manipulable button or pad.

Figure 4:
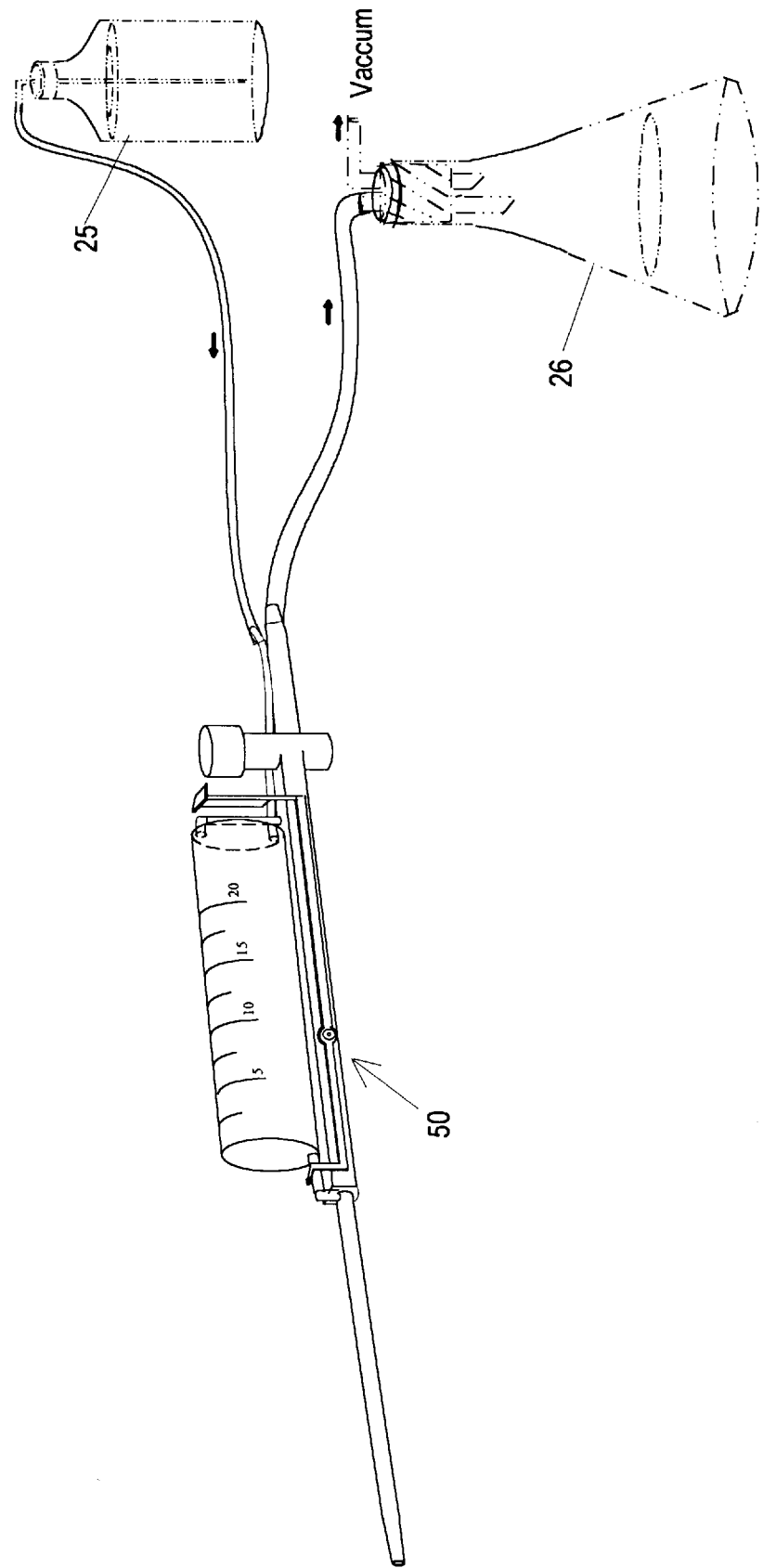
FIG. 4 is a perspective view of the FIG. 1 apparatus connected to containers which do not form a part of the present invention.

Operation of the apparatus 1 is best illustrated in FIG. 4. By connecting the device to a "clean" medium container 25 via the tubing 7, which is preferably sterile, and connecting the opening 9 to a waste collecting bottle 26 which is ultimately connected to a vacuum source, the process can begin. The method for transferring the fluids is described as follows:

1) Hold the apparatus 1 with one hand and immerse the opening tip 8 into the old liquid which is intended to be disposed. Flow cannot occur since tubing 5 is clamped closed and the pipe 1 is open to atmosphere through the forward channel 17. Equally apparent is that the vacuum cannot be utilized since the rearward channel 17 is also open to the atmosphere.

2) Push the seal cap 21 downward until it seats upon the housing 3 thereby causing the passage 20 to align with the inside of the pipe 1. At this point both the pipe 1 and the reservoir 2 are under vacuum. Flow is established through the pipe 1 from the opening tip 8, out opening 9 into the waste collection bottle 26.

3) Simultaneously vacuum is applied to the clean medium container 25 through the tubing 6, the reservoir 2, and the tubing 7 thus filling the reservoir 2 with clean liquid.

4) Under normal circumstances suction is maintained until either one of the following occurs: the seal cap 21 is released, or the opening tip 8 is removed from the liquid or the liquid is completely suctioned from its container.

5) Once the old medium is removed and the reservoir 2 is filled, depressing the paddle 24 causes the forward portion 22 of the lever 36 to pivot about the pin connection 37 thereby unclamping the tubing 5 thus emptying the reservoir 2 into the now emptied container or culture vessel.

Placement of the opening 14 higher in the cylinder reservoir 2 prevents old medium from entering the reservoir during the vacuum process while also eliminating the inadvertent disposal of the clean liquid unless the reservoir 2 overfills. As should be apparent, the apparatus and the method with which it is used greatly simplifies the task of changing liquid mediums. Other options which may be desirable are to provide graduation markings 12 on the cylinder reservoir 2 so as to accurately control the volume of liquid added to the culture. Additionally, the opening tip 8 can be made to be replaceable. This may be desirable if it is required that no cross contamination occur between the old liquid and the new. Of course, a number of options exist regarding the opening tip design whether it is replaceable or not. For instance two opening tips, as depicted in FIG. 5, could be provided, one for the aspiration process configured as already described and a second tip 60 to which the tube 5 connects. The tube 5 would now be isolated from the first tip 8 and connected directly to the second tip 60. To prevent contamination of the second tip 60 during the aspiration process, many options exist including making the second tip vertically coplanar with respect to the first tip but shorter. Other possibilities can also be envisioned by those skilled in the art and consequently are considered a part of this invention as well.

As such the method of making and using the device detailed above constitute the inventor's preferred embodiment and alternate embodiments to the invention. The inventor is aware that numerous configurations of the device as a whole or some of its constituent parts are available which would provide the desired results. While the invention has been described and illustrated with reference to specific embodiments, it is understood that these other embodiments may be resorted to without departing from the invention. Therefore the form of the invention set out above should be considered illustrative and not as limiting the scope of the following claims.

What is claimed is:

1. A liquid medium exchange device comprising:

a vacuum control for engaging and disengaging a vacuum source;

a pipe having a first and a second end, said first end connected to said vacuum control and said second end for immersion in a liquid destined for disposal; and a reservoir attachably and detachably connected to a replacement liquid source for temporary storage of a liquid from said replacement liquid source therein, said reservoir further connected to said vacuum control;

wherein manipulation of said vacuum control in a first position subjects said second end of said pipe and said reservoir to said vacuum source thereby evacuating said liquid destined for disposal through said pipe and simultaneously drawing said replacement liquid source into said reservoir.

2. The liquid medium exchange device of claim 1 further comprising means for dispensing said replacement liquid from said reservoir.

3. The liquid medium exchange device of claim 1 wherein said means for dispensing said replacement liquid from said reservoir is via said second end of said pipe.

4. The liquid medium exchange device of claim 1 further comprising a second pipe attached at one end to said reservoir providing a means for dispensing said replacement liquid from said reservoir.

5. The liquid medium exchange device of claim 1 further comprising:

a passageway having a first end connected to said reservoir and a second end connected to said pipe, said passageway enabling transfer of said replacement liquid from said reservoir to said second end of said pipe;

a means for opening and closing said passageway.

6. A liquid medium exchange apparatus comprising:

a pipe having a first open end and a second open end, said second open end adapted to connect to a vacuum source, said pipe further comprising a first and a second opening, each radially disposed upon said pipe's exterior surface and extending through a sidewall of said pipe from said exterior surface to said pipe's interior surface;

a liquid reservoir having a plurality of reservoir openings therein, wherein at least a first reservoir opening is connected to a first liquid source, and at least a second reservoir opening is connected to said vacuum source by way of said second opening in said pipe thereby enabling a liquid from said first liquid source to flow into said reservoir under vacuum, and at least a third reservoir opening is connected to said first opening in said pipe which allows said liquid to be drained from said reservoir; and a vacuum controller disposed between said second open end of said pipe and said second reservoir opening for alternately engaging and disengaging vacuum as desired by an operator.

7. The liquid medium exchange apparatus of claim 6 wherein said means which allows said liquid to be drained from said reservoir comprises an operator manipulable reservoir control.

8. The liquid medium exchange apparatus of claim 7 wherein said operator manipulable reservoir control comprises:

a soft collapsible length of tubing disposed between and forming a passageway from said third reservoir opening to said first opening in said pipe;

a lever disposed across said tubing, said lever clamping said tubing against a clamping surface thereby effectively eliminating flow through said tubing; and means for enabling said operator to unclamp said lever thereby allowing liquid flow through said tubing.

9. The liquid medium exchange apparatus of claim 6 wherein said vacuum controller further comprises:

a housing open to atmosphere, said housing further being divided into two channels by a dividing wall;

a seal cap adapted to seat upon and seal said housing from said atmosphere;

a partition attached to said seal cap disposed inwardly into said housing to slidingly interact with said dividing wall, said partition further comprising a passage therethrough; and a biasing means for holding said seal cap off of said housing in a normally open position, said biasing means able to be held by said operator in a closed position thereby simultaneously seating said seal cap upon said housing and aligning said passage in said partition with said interior surface of said pipe, said closed position subjecting said reservoir and said pipe to said vacuum.

10. The liquid medium exchange apparatus of claim 9 wherein said biasing means is a spring.

11. The liquid medium exchange apparatus of claim 6 wherein said first open end of said pipe is disconnectable and disposable.

12. The liquid medium exchange apparatus of claim 6 wherein said reservoir further comprises volumetric indicia.

13. A liquid medium exchange apparatus comprising:

a pipe having a first open end and a second open end, said pipe further comprising at least a first and a second opening, each radially disposed upon said pipe's exterior surface and extending through a sidewall of said pipe from said exterior surface to said pipe's interior surface;

a liquid reservoir having a plurality of reservoir openings therein, wherein said plurality of reservoir openings further comprise at least, a first reservoir opening, a second reservoir opening connected to said second opening in said pipe, and a third reservoir opening connected to said first opening in said pipe.

a vacuum controller disposed between said second open end in said pipe and a vacuum source for alternately engaging and disengaging vacuum as desired by an operator, wherein engaging vacuum enables a first liquid to be suctioned into said reservoir through said first reservoir opening while enabling a second liquid to be suctioned into said first open end of said pipe, through said pipe, and out said second open end of said pipe; and a reservoir control disposed between said third reservoir opening and said first opening in said pipe, said reservoir control capable of being alternately opened and closed by said operator; wherein said reservoir control is in a normally closed position and opening said reservoir control allows said first liquid to exit said reservoir, enter said pipe, and exit said pipe through said first open end of said pipe.

14. The liquid medium exchange apparatus of claim 13 wherein said vacuum controller further comprises:

a housing open to atmosphere, said housing further being divided into two channels by a dividing wall;

a seal cap adapted to seat upon and seal said housing from said atmosphere;

a partition attached to said seal cap disposed inwardly into said housing to slidingly interact with said dividing wall, said partition further comprising a passage therethrough; and a biasing means for holding said seal cap off of said housing in a first normally open position, said biasing means able to be held by said operator in a second closed position thereby simultaneously seating said seal cap upon said housing and aligning said passage in said partition with said interior surface of said pipe, said closed position subjecting said reservoir and said pipe to said vacuum.

15. The liquid medium exchange apparatus of claim 14 wherein said biasing means is a spring.

16. The liquid medium exchange apparatus of claim 13 wherein said reservoir control comprises:

a soft collapsible length of tubing connecting said third reservoir opening to said first opening in said pipe;

a lever disposed across said tubing, said lever clamping said tubing against a clamping surface thereby effectively eliminating flow through said tubing; and means for enabling said operator to unclamp said lever thereby allowing liquid flow through said tubing.

17. The liquid medium exchange apparatus of claim 13 wherein said first open end of said pipe is disconnectable and disposable.

18. The liquid medium exchange apparatus of claim 13 wherein said reservoir further comprises volumetric indicia.

* * * * *